United States Patent [19]
Li

[11] Patent Number: 6,124,462
[45] Date of Patent: Sep. 26, 2000

[54] CATALYSIS USING PHOSPHINE OXIDE COMPOUNDS

[75] Inventor: George Y. Li, Wilmington, Del.

[73] Assignee: E. I. du Pont de Nemours and Company, Wilmington, Del.

[21] Appl. No.: 09/451,150

[22] Filed: Nov. 30, 1999

[51] Int. Cl.⁷ .................................................. C07D 211/00
[52] U.S. Cl. ......................... 546/184; 564/433; 568/642; 568/643; 585/457; 585/466
[58] Field of Search ............................ 546/184; 504/433; 568/642, 643; 585/466, 457

[56] References Cited

U.S. PATENT DOCUMENTS 5,756,804  5/1998  Haber et al. .............................. 558/411
5,801,263  9/1998  Seitz et al. ............................... 558/155

OTHER PUBLICATIONS

Chem Abstracts, 1997:297209, Hartwig, John, Synlett (1997), 4, 329–340, month unavailable.
Chem Abstracts 1999:297603, Suzuki, Akira, J. Organomet. Chem. 1999, 576 (1–2), 147–168, month unavailable.
Hartwig, SYNLETT, 1997, (4), pp. 329–340.
Suzuki, A., J. Orgmet. Chem., 576 (1999) p. 305.
Genet, J. Organomet. Chem., 576 (1999) p. 305.

*Primary Examiner*—Samuel Barts

[57] ABSTRACT

Phosphine oxide compounds were used with transition metals, preferably palladium, to produce biaryls and arylamines via cross-coupling reactions with aryl halides and arylboronic acids or amines.

15 Claims, No Drawings

CATALYSIS USING PHOSPHINE OXIDE COMPOUNDS

FIELD OF INVENTION

The invention relates to the use of phosphine oxide compounds complexed with transition metals to produce biaryls and arylamines via cross-coupling reactions with aryl halides and arylboronic acids or amines.

BACKGROUND

Chelating phosphine compounds when bound to metal atoms are generally known to be useful as catalysts. One reaction which uses palladium phosphine catalysts is the coupling of aryl halides with amines for the production of arylamines, as reviewed by Hartwig, SYNLETT, 1997, (4), pg. 329–340. An example of this reaction is the coupling of chlorobenzene and piperidine to form N-phenylpiperidine:

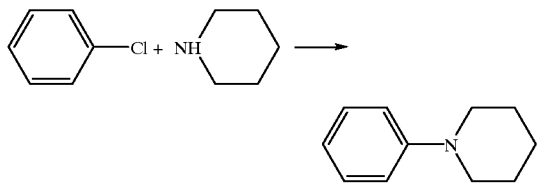

Another reaction in which palldium/phosphine catalysts have been used is the Suzuki reaction, where biaryls are produced through the coupling of arylboronic acids and aryl halides, as reviewed by Suzuki, A, J. Orgmet. Chem., 576 (1999), pg. 147. One example of this reaction is the preparation of biphenyl from phenylboronic acid and chlorobenzene:

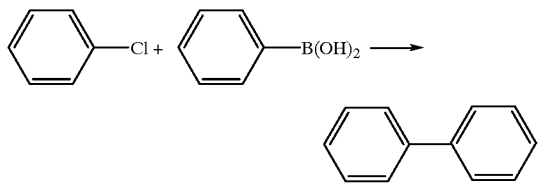

Both of these products are important classes of compounds widely used in the manufacture of pharmaceuticals, advanced materials, liquid polymers and ligands, and much work has been done on their preparation. However, there is an expanding need for stable, easily prepared catalysts that result in good yields and mild reaction conditions.

Preparation of new ligands has traditionally been performed one at a time after tedious synthesis and purification protocols. Combinatorial techniques have greatly accelerated the discovery of new ligands, but new synthetic schemes are needed. One valuable technique uses solid-phase supports. This solid-phase protocol allows reactions on a polymer-bound scaffold to be driven to completion by using large excesses of reagents in solution that can be easily filtered away from the polymer support. After the scaffold has been modified, an additional cleavage step then frees the small molecule from the polymer support into solution for isolation.

Phosphine oxide compounds and libraries have been prepared using polymer scaffolds in U.S. application Ser. No. 09/415,347 (U.S. Ser. No. 99/23509) which is incorporated in its entirety by reference. Lacking is a process for the convenient preparation of stable arylamines of the formula $R^1$—$NR^2R^3$ or biaryls of the formula $R^1$–$R^6$ using a stable phosphine catalyst under mild conditions and producing good yields.

SUMMARY OF THE INVENTION

This invention is directed to the use of phosphine oxide compounds complexed with transition metals to produce biaryls and arylamines via cross-coupling reactions with aryl halides and arylboronic acids or amines.

More specifically, the invention is directed to a process to prepare arylamines of the formula $R^1$—$NR^2R^3$ comprising contacting an arnine of the formula $HNR^2R^3$ with an aryl compound of the formula $R^1$—$X$ in the presence of a catalytic amount of a coordination compound comprising one or more transition metals complexed to a phosphine oxide ligand of the formula $HP(O)R^4R^5$; wherein X is a halogen; $R^1$ is an optionally substituted aryl; $R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

Preferably, $R^1$ is an optionally substituted phenyl, and the transition metal is selected from Periodic Group VIII. More preferably, $R^4$ and $R^5$ are independently selected from the group consisting of hydrocarbyl, substituted hydrocarbyl and heterocyclic, the transition metal is Pd, and $R^2$ and $R^3$ are selected from the group consisting of hydrogen, optionally substituted aryl, and wherein $R^2$ and $R^3$ are hydrocarbyl and together form a ring. Most preferably X is Cl, $R^1$ is selected from the group consisting of phenyl, 4-methylphenyl, 4-methoxyphenyl, and 4-trifluoromethylphenyl; $R^2$ and $R^3$ are selected from the group consisting of hydrogen, phenyl, 4-methylphenyl, and together form a piperidyl ring; and $R^4$ and $R^5$ are selected from the group consisting of t-butyl, phenyl, i-propyl, and 2,4-methoxyphenyl.

The invention is further directed to a process to prepare biaryls of the formula $R^1$–$R^6$ comprising contacting a boronic acid of the formula $R^6$—$B(OH)_2$ with an aryl compound of the formula $R^1$—$X$ in the presence of a catalytic amount of a coordination compound comprising one or more transition metals complexed to a phosphine oxide ligand of the formula $HP(O)R^4R^5$ wherein X is a halogen; $R^1$ is an optionally substituted aryl; $R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

Preferably $R^1$ is an optionally substituted phenyl, and the transition metal is selected from Periodic Group VIII. More preferably $R^4$ and $R^5$ are independently selected from the group consisting of hydrocarbyl, substituted hydrocarbyl and heterocyclic, the transition metal is Pd, and $R^6$ is an optionally substituted aryl. Most preferably X is Cl, $R^1$ is selected from the group consisting of of phenyl, 4-methoxyphenyl, 2-methoxyphenyl and 4-methylphenyl; $R^6$ is selected from the group consisting of 4-methoxyphenyl, and phenyl; and $R^4$ and $R^5$ are selected from the group consisting of t-butyl, phenyl, i-propyl, and 2,4-methoxyphenyl.

Further, the invention includes the method of using phosphine oxides as ligands for homogeneous catalysis of arylamines of the formula $R^1$—$NR^2R^3$ or biaryls of the formula $R^1$–$R^6$ comprising (1) preparing a coordination compound comprising one or more transition metals complexed to a phosphine oxide compound of the formula $HP(O)R^4R^5$, wherein X is a halogen; $R^1$ is an optionally substituted aryl; $R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring; and (2) contacting either (i) a boronic acid of the formula $R^6$—$B(OH)_2$ or (ii) an amine of the formula $HNR^2R^3$ with an aryl compound of the formula $R^1$—X in the presence of a catalytic amount of the coordination compound prepared in step (1) to form, respectively, arylamines of the formula $R^1$—$NR^2R^3$ or biaryls of the formula $R^1$–$R^6$.

DETAILED DESCRIPTION OF THE INVENTION

This disclosure sets out methods for the use of phosphine oxide compounds complexed with transition metals to produce biaryls and arylamines via cross-coupling reactions with aryl halides and arylboronic acids or amines. Phosphine oxides were not previously used as ligands in homogeneous catalysis, primarily because the P-atoms do not have coordinated atoms with lone-pair electrons which were considered essential.

The processes of the instant invention are an improvement over similar processes in the art. The phosphine oxide compounds used in the instant processes are air-stable solids and are easily handled, and can be easily synthesized in a variety of forms using the methods described in U.S. patent application Ser. No. 09/415,347 (U.S. Ser. No. 99/23509). The processes are easily adapted to combinatorial procedures and can be used to construct libraries of biaryls and arylamines, which are themselves widely used in the manufacture of pharmaceuticals, advanced materials, liquid polymers and as ligands. Two examples of compounds or derivatives thereof that could be made by these processes are the synthetic dye Quinizarin Green and p-aminobiphenyl, used as an antioxidant.

Phosphine Oxide Compounds and Libraries

Phosphine oxide compounds of the formula $HP(O)R^4R^5$ are known to exist in two tautomeric forms:

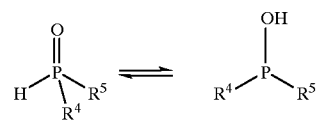

The phosphine oxide compounds can be prepared by any method. One such method is via the use of polymer scaffolds as described in U.S. application Ser. No. 09/415,347 (U.S. Ser. No. 99/23509), herein incorporated by reference. This scheme comprises the steps of contacting (i) a phosphine selected from the group consisting of $XPR^4R^5$ and $HP(=O)R^4R^5$, wherein X is a halogen, and $R^4R^5$ are independently selected from the group consisting of hydrocarbyl, substituted hydrocarbyl and heterocyclic, organometallic, Cl, Br, I, $SQ_1$, $OQ_2$, $PQ_3Q_4$ and $NQ_5Q_6$, when $Q_1$, $Q_2$, $Q_3$, $Q_4$, $Q_5$ and $Q_6$ are independently selected from the group consisting of hydrogen, hydrocarbyl, substituted hydrocarbyl, hydrocarbyl amino, alkoxy, aryloxy, and heterocyclic, and optionally $R^4$ and $R^5$ can together form a ring, with (ii) a solid support, resulting in at least one P in the phosphine attached indirectly or directly to the solid support via one or more covalent bonds, and optionally replacing one or more of $R^4$ and $R^5$ with any other $R^4$ and $R^5$ defined above.

Virtually any solid material may be used as a support to prepare the phosphine oxide compounds provided it meets the following criteria:

The material is insoluble in organic, aqueous, or inorganic solvents. Organic polymer supports are acceptable in this regard but they generally need to be crosslinked. Inorganic support, such as metal oxides ($SiO_2$, $Al_2O_3$, $TiO_2$, $ZrO_2$, etc.), clays, and zeolites, and modified carbons are generally insoluble in these solvents and also may be used as supports.

The support contains reactive sites, which can be used for the covalent attachment of the phosphorus.

The reactive sites are isolated to prevent additional crosslinking during further chemical transformations.

The reactive sites are exposed to the reaction medium. With a polymer resin support this is achieved through the use of a resin which swells in a reaction solvent or is sufficiently porous to allow transport of the reaction medium through the polymer matrix.

The term solid support refers to a material having a rigid or semi-rigid surface that contains or can be derivatized to contain functionality, which covalently links a compound to the surface thereof. Other modifications may be made in order to achieve desired physical properties. Such materials are well known in the art and include, by way of example, polystyrene supports, polyacrylamide supports, polyethyleneglycol supports, metal oxides such as silica, and the like. Such supports will preferably take the form of small beads, pellets, disks, films, or other conventional forms, although other forms may be used.

A preferred solid support is an organic or inorganic polymer to which the phosphorus can be covalently attached through a side chain or pendant group of the polymeric backbone. The polymer may be crosslinked or modified. Suitable preferred polymers useful in the preparation of a supported phosphine compound or a combinatorial library of supported phosphine compounds includes polyolefins, polyacrylates, polymethacrylates, and copolymers thereof that meet the general criteria described above. A more preferred polymeric support is polystyrene wherein the phosphorus is attached to a pendant phenyl group on the polystyrene backbone. Most preferred is polystyrene, crosslinked with divinylbenzene. Specifically, polystyrenes commonly used for solid phase synthesis have been used. These particular resins are crosslinked with from 1 to 10 wt % divinylbenzene. The styrene moieties are substituted in the para or meta positions. Only a portion of the styrene moieties are substituted, typically resulting in functional group loadings of approximately 0.2 to 2.0 mmole per gram of resin, although this value may be higher or lower.

A combinatorial library of phosphine oxides can be used in the instant invention as well as single compounds. To create a library, one or more phosphines are reacted with one or more solid supports, generating a plurality of supported phosphine compounds. Alternatively, a library may be created by reacting one supported phosphine compound with a plurality of cleaving agents, as described below.

As used herein, a combinatorial library is an intentionally created collection of a plurality of differing molecules which can be prepared by selected synthetic means and screened for a desired activity or characteristic in a variety of formats (e.g., libraries of soluble molecules, libraries of compounds attached to resin beads, silica chips, or other solid supports). The libraries are generally prepared such that the compounds are in approximately equimolar quantities, and are prepared by combinatorial synthesis. Combinatorial synthesis refers to the parallel synthesis of diverse compounds by sequential additions of multiple choices of reagents which leads to the generation of large chemical libraries containing related molecules having molecular diversity. Screening methods for libraries vary greatly and are dependent upon a desired activity, the size of library, and the class of compounds in the library.

The libraries can be of any type. These types include but are not limited to arrays and mixtures. Arrays are libraries in which the individual compounds are simultaneously synthesized in spatially segregated locations, typically identified by their location on a grid. Mixture libraries contain a mixture of compounds that are simultaneously synthesized and assayed. Identification of the most active compound is then performed by any of several techniques well known in the combinatorial art, such as deconvolution. (*Proc. Natl. Acad. Sci. USA*, 91, pg. 10779 (1994)).

A preferred solid support for the combinatorial libraries of the instant invention is an organic or inorganic polymer as described above, to which the phosphorus can be covalently attached through a side chain or pendant group of the polymeric backbone.

One scheme used in attaching the P to the solid support is via the reaction of the halogen or hydrogen bonded to the phosphorus in the phosphine with a nucleophilic group that is covalently attached to a solid support. The term nucleophilic group is well recognized in the art and refers to chemical moieties having a reactive pair of electrons. This scheme can easily be adapted for combinatorial synthesis.

Examples of reactions to prepare the phosphine oxide compounds are shown but not limited to those in Scheme 1 below, where SS is the solid support, X is a halogen, M is any metal, R can be one or more of $R^4$ or $R^5$ as defined above, Z is a divalent attaching group covalently attached to at least one phosphorus in the phosphine, selected from the group consisting of hydrocarbylene, substituted hydrocarbylene, —O—, —S—, and —NR'—, where R' is selected from the group consisting of an optionally-substituted hydrocarbyl and halogen, and the Z, O, S, and N substituents are covalently attached to the solid support.

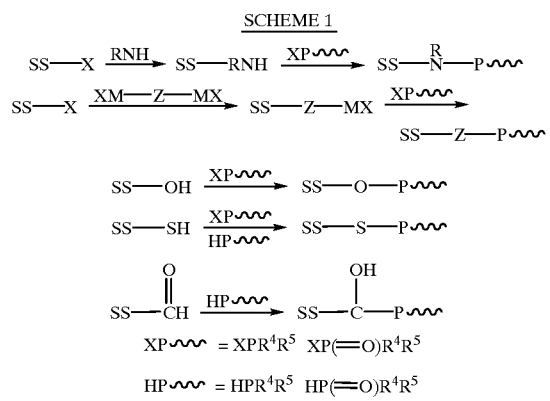

SCHEME 1

Any of the substituents in the above compounds may be replaced by other functional groups using any procedure known in the art. One or all of the substituents can be reacted in a single reaction, depending on the choice of reactants and reaction conditions. These reactions can easily be adapted for combinatorial processes. Examples of suitable procedures are shown by but not limited to those depicted in Scheme 2 below, where X, and M are as defined above, and R indicates any of $R^4$ or $R^5$, as defined above. Examples of suitable definitions for M include Mg, Li, and Zn. Cp indicates a cyclopentadienyl ring.

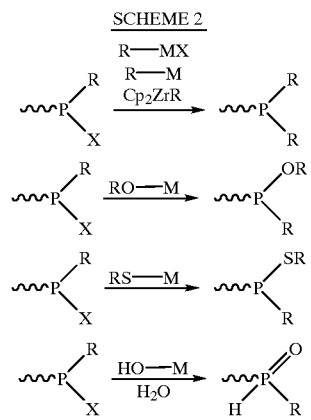

SCHEME 2

The phosphine oxide compounds are formed by cleaving the compound from the solid support by contacting the supported phosphine with a compound of the Formula ER", wherein E is an electrophilic group and R" is selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle. R" can be optionally replaced by any of $R^4$ or $R^5$. To create a library, one or more supported phosphines are reacted with one or more compounds of the Formula ER", generating a plurality of phosphine compounds.

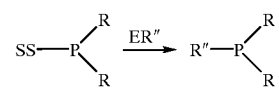

In the above process, E is any electrophilic group that will cleave the covalent bond attaching the phosphorus to the solid support. The term electrophilic group is a term well recognized in the art and refers to chemical moieties, which can accept a pair of electrons from a nucleophilic group as defined above. Suitable electrophilic groups include H, trimethylsilyl, $PCl_2$, halogens, and protons donated from compounds such as acids, alcohols, or amines.

In the instance where $ER_5$ is water, the resulting POH group would rearrange to yield to form the phosphine oxide compounds used in the instant invention. These compounds can also be formed from any other phosphine of the formula $RPR^4R^5$ via the replacement of R with an —OH group using any method known in the art. An equivalent rearrangement occurs when a PSH group is present.

Another method for preparing the phosphine oxide compounds is to prepare a phosphine oxide attached to the solid support, as explained above, then to cleave the phosphine oxide directly from the solid support.

After cleavage from the solid support, $R^4$ and $R^5$ may be replaced with any other substituent using any method known in the art, in order to prepare a further range of compounds, such as those described in *Encyclopedia of Inorganic Chemistry* (John Wiley & Sons, Vol. 6, pg. 3149–3213).

Reactions of Amines with Aryl Halides to Prepared Arylamines of the Formula $NHR^2R^3$ A process is described to prepare arylamines of the formula $R^1$—$NR^2R^3$ comprising contacting an amine of the formula $HNR^2R^3$ with an aryl compound of the formula $R^1$—X in the presence of a catalytic amount of a coordination compound comprising one or more transition metals complexed to a phosphine oxide compound of the formula $HP(O)R^4R^5$.

In this process, X is a halogen, $R^1$ is an optionally substituted aryl radical, $R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring, and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$ and $NQ_5Q_6$, where $Q_1$, $Q_2$, $Q_3$, $Q_4$, $Q_5$ and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring. Optionally, the process can be performed intramolecularly; i.e. the amine functionality and the aryl functionality are both located on the same compound and the process results in a cyclization.

The amine and the aryl compound can be prepared by any method, including any of the well-known processes in the art.

"Coordination compound" refers to a compound formed by the union of a metal ion (usually a transition metal) with a non-metallic ion or molecule called a ligand or complexing agent.

The transition metals are defined as metals of atomic weight 21 through 83. Preferably, the transition metal is from Periodic Group VIII (defined as Fe, Co, Ni, Ru, Rh, Pd, Os, Ir, and Pt). More preferred is Pd. The complex can be made by any synthetic method known in the art, either through direct reaction or via the use of a transition metal precursor.

The phosphine oxide compound is prepared as disclosed above. The phosphine oxide used in the instant invention can exist in either tautomeric form when present as a component of the complex. The complex can be isolated and purified before use, or be prepared and used in situ. Many of these techniques are described in Hartley, F. R. (Ed), "*Chem. Met.—Carbon Bond*", 1987, vol. 4, pp. 1163–1225).

By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methyl-cyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include methoxy, phenoxy, toluyl, chlorobenzyl, fluoroethyl, p-$CH_3$—S—$C_6H_5$, 2-methoxypropyl, and $(CH_3)_3SiCH_2$.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. By aryl is also meant heteroaryl groups where heteroaryl is defined as 5-, 6-, or 7-membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

A preferred process is where $R^1$ is an optionally substituted phenyl, $R^4$ and $R^5$ are independently selected from the group consisting of hydrocarbyl, substituted hydrocarbyl and heterocyclic, and where $R^2$ and $R^3$ are selected from the group consisting of hydrogen, optionally substituted aryl, and where $R^2$ and $R^3$ are hydrocarbyl and together form a ring. More preferred is where X is Cl, $R^1$ is selected from the group consisting of phenyl, 4-methylphenyl, 4-methoxyphenyl and 4-trifluoromethylphenyl, $R^2$ and $R^3$ are selected from the group consisting of hydrogen, phenyl, 4-methylphenyl, and together form a piperidyl ring, and $R^4$ and $R^5$ are selected from the group consisting of t-butyl, phenyl, i-propyl, and 2,4-methoxyphenyl. Also preferably, the transition metal is from Periodic Group VIII. More preferred is Pd.

Reactions of Arylboronic Acids with Aryl Halides to Prepare Biaryls of the Formula $R^1$–$R^6$ The instant invention also describes a process to prepare biaryls of the formula $R^1$–$R^6$ comprising contacting a boronic acid of the formula $R^6$—$B(OH)_2$ with an aryl compound of the formula $R^1$—X in the presence of a catalytic amount of a coordination compound comprising one or more transition metals complexed to a phosphine oxide compound of the formula $HP(O)R^4R^5$; where X is a halogen, $R^1$ is an optionally substituted aryl, $R^6$ is selected from the group consisting of hydrocarbyl, substituted hydrocarbyl, hydrocarbylamino, alkoxy, aryloxy, and heterocyclic, and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring. Optionally, the process can be performed intramolecularly; i.e., the boronic acid functionality and the aryl functionality are both located on the same compound and the process results in a cyclization.

A preferred process is where $R^1$ is an optionally substituted phenyl, $R^4$ and $R^5$ are independently selected from the group consisting of hydrocarbyl, substituted hydrocarbyl and heterocyclic, and where $R^6$ is an optionally substituted aryl. More preferred is where X is Cl, $R^1$ is selected from the group consisting of of phenyl, 4-methoxyphenyl, 2-methoxyphenyl and 4-methylphenyl; $R^6$ is selected from the group consisting of 4-methoxyphenyl, and phenyl; and $R^4$ and $R^5$ are selected from the group consisting of t-butyl, phenyl, i-propyl, and 2,4-methoxyphenyl. Also preferably, the transition metal is from Periodic Group VIII. More preferred is Pd.

Schemes 1 and 2 to form phosphine oxides, the cleaving procedures, and the coupling reactions disclosed above are preferably performed under dry, inert atmosphere with dry, deoxygenated solvents. Any solvent is suitable provided that it is inert to all reagents and products. Suitable temperatures for homogeneous catalysis range from −80° C. to 200° C. Preferred temperatures are about 0° C. to about 150° C. Preferably a base should be added in both coupling reactions disclosed. Preferred bases are CsF, $CsCO_3$, and NaOtBu.

The following non-limiting Examples are meant to illustrate the invention but are not intended to limit it in any way.

Materials and Methods

All manipulations of air-sensitive materials were carried out with rigorous exclusion of oxygen and moisture in flame-dried Schlenk-type glassware on a dual manifold Schlenk line, interfaced to a high-vacuum ($10^{-4}$–$10^{-5}$ Torr) line, or in a nitrogen-filled Vacuum Atmospheres glovebox with a high-capacity recirculator (1–2 ppm of $O_2$). Before use, all solvents were distilled under dry nitrogen over appropriate drying agents (such as sodium benzophenone ketyl and metal hydrides except for chlorinated solvents). Deuterium oxide, THF-$D_8$, $C_6D_6$ and chloroform-d were purchased from Cambridge Isotopes (Andover, Mass.). All organic and inorganic starting materials were purchased from Aldrich Chemical Co. (Milwaukee Wis.), Farchan Laboratories Inc. (Gainesville, Fla.), Strem Chemicals (Newburyport, Mass.), Calbiochem-NovaBiochem Corp. (San Diego, Calif.), Rieke Metals, Inc. (Lincoln, Neb.), or Lancaster Synthesis Inc. (Windham, N.H.), and when appropriate were distilled prior to use.

| List of abbreviations | |
|---|---|
| dba | Bis(dibenzylideneacetone) |
| DVB | Divinylbenzene |
| GC/MS | Gas chromatography/mass spectroscopy |
| FT | Fourier transform |
| h | Hour |
| i.d | Inner diameter |
| in. | Inch |
| Me | Methyl |
| mg | milligram |
| NMR | Nuclear magnetic resonance |
| tBu | tert-butyl |

Physical and Analytical Measurements

NMR spectra were recorded on either a Nicolet NMC-300 wide-bore (FT, 300 MHz, $^1H$; 75 MHz, $^{13}C$, 121 MHz $^{31}P$), or GE QM-300 narrow-bore (FT, 300 MHz, $^1H$) instrument. Chemical shifts (δ) for $^1H$, $^{13}C$ are referenced to internal solvent resonances and reported relative to $SiMe_4$. $^{31}P$ NMR shifts are reported relative to external phosphoric acid. Analytical gas chromatography was performed on a Varian Model 3700 gas chromatograph with FID detectors and a Hewlett-Packard 3390A digital recorder/integrator using a 0.125 in. i.d. column with 3.8% w/w SE-30 liquid phase on Chromosorb W support. GC/MS studies were conducted on a VG 70-250 SE instrument with 70 eV electron impact ionization.

The polymer bound monophosphines were prepared as described in U.S. patent application No. 09/415,347 (U.S. Ser. No. 99/23509). The functional groups on the phosphines can be added in two steps to yield unsymmetrical substitutions, or in one step to yield more symmetrical substitution.

A solution of t-butylamine (276 g, 3.78 moles) and KI (0.3 g, 2 mmol) in 1000 mL of THF was treated with chloromethylpolystyrene-divinylbenzene (Merrifield resin, 2% DVB, 75 g, 1.26 mmol/g, 94.5 mmol) while stirring at room temperature for 30 min. The suspension was then refluxed for 24 h before the solution was filtered off. The resulting resin was washed with $H_2O$ (3×250 mL), THF (3×150 mL), then hexane (3×200 mL). After drying in vacuum overnight, 75 g of the resin were obtained (98% yield according to N elemental analysis. Anal. calculated for polymer-NHC(Me)$_3$: N, 1.25. Found: N, 1.22). Also the disappearance of $^1H$ resonances of polymer-Ph—$CH_2$—Cl ($CH_2$=~4.5 ppm) and the appearance of $^1H$ resonances of polymer-Ph—$CH_2$—NHC(Me)$_3$ ($CH_2$=~3.7 ppm) indicates that the chloromethyl groups were completely transformed to tert-butylaminometyl groups. Hereafter this will be referred to as Resin I.

A solution of $PCl_3$ (26 g, 189 mmol) in 400 mL of THF was treated slowly with Resin I from above (25 g, 1.21 mmol/g, 30.3 mmol) while stirring at room temperature for a period of 30 min. before $Et_3N$ (16 g, 157.5 mmol) was added. The resulting suspension was stirred at room temperature overnight before the solution was filtered off. The resin was washed with hexane (2×50 mL), $CH_2Cl_2$ (5×80 mL), and hexane (5×30 mL). The resulting polymer-bound $PCl_3$ resin was dried in vacuum overnight. $^{31}P$ NMR (122 MHz, $CDCl_3$): δ 179.1 ppm.

A suspension of the polymer-bound $PCl_2$ resin from above (5.0 g, 1.12 mmol/g, 5.6 mmol) in 150 mL of THF was treated slowly with phenylmagnesium bromide (2 M solution in diethylether, 64 mmol). The resulting mixture was stirred at room temperature for 30 min. before the solution was filtered off and the resin was washed with THF (3×50 ml), $Me_2CHOH$/THF (20% $Me_2CHOH$, 10 mL), hexane (3×30 mL). The resulting resin was dried in vacuum overnight to yield polymer-bound $PPh_2$. $^{31}P$ NMR (122 MHz, $CDCl_3$): δ 52.3 ppm.

A solution of $Cl_2PPh$ (33.8 g, 189 mmol) and $Et_3N$ (16.0 g, 157.5 mmol) in 500 mL of THF was treated slowly with Resin I (25.0 g, 1.21 mmol/g, 30.3 mmol) while stirring at room temperature for a period of 10 min. The resulting suspension was stirred at room temperature overnight before the solution was filtered off. The resin was washed with THF (50 mL), hexane (3×50 mL), $CH_2Cl_2$ (4×50 mL), and hexane (2×50 mL). The resulting polymer-bound PPhCl resin was dried in vacuum overnight. $^{31}P$ NMR (122 MHz, $CDCl_3$): δ 135.4 ppm.

A suspension of the resulting resin, the polymer-bound PPhCl, (5.0 g, 1.03 mmol/g, 5.2 mmol) in 150 mL of THF was treated slowly with i-propylmagnesium chloride (0.5 M solution in diethylether, 32.0 mmol). The resulting mixture was stirred at room temperature for 2 h before the solution was filtered off and the resin was washed with THF (3×10 mL), $Me_2CHOH/THF$ (20% $Me_2CHOH$, 5 mL), hexane (3×30 mL). The resulting resin was dried in vacuum overnight to afford polymer-bound (i-$C_3H_7$)PPh. $^{31}P$ NMR (122 MHz, $CDCl_3$): δ 55.5 ppm.

The following Experiments illustrate the preparation of the phosphine oxide catalyst used in the method.

Experiment 1

Synthesis of ($Me_2CH$)PH(O)(Ph)

A suspension of polymer-bound PPh($CHMe_2$) prepared as described above (1.25 g, 1.02 mmol/g, 1.28 mmol, $^{31}P$ NMR (121 MHz, $CDCl_3$): δ 55.5 ppm) and $H_2O$ (0.1 g, 4.8 mmol) in THF (10 mL) was refluxed overnight before the resin was filtered off and washed with THF (2×5 mL). The filtrate was dried under vacuum to remove the solvent and excess $H_2O$. The resulting residue was 80 mg (37% yield) of ($Me_2CH$)PH(O)(Ph). It was >95% pure by $^1H$ NMR and GC/MS. $^{31}P$ NMR (121 MHz, $CDCl_3$, $^1H$-decoupled): δ 47.8. $^{31}P$ NMR (121 MHz, $CDCl_3$, $^1H$-coupled): δ 47.8 (d, $J_{p\text{-}H}$=487.7 Hz). $^1H$ NMR (500 MHz, $CDCl_3$): δ 7.74–7.53 (m, 5H), 7.25 (d, $J_{p\text{-}H}$=487.5 Hz, 1H), 2.33 (m, 1H), 1.12 (m, 6H). $^{13}C$ NMR (125 MHz, $CDCl_3$): δ 133.8, 131.1, 129.4, 125.4, 28.0, 14.7. HRMS: Calculated for $C_9H_{13}PO(M^+)$: 168.0704. Found: 168.0704.

Experiment 2

Synthesis of ($Me_3C$)PH(O)($CMe_3$)

A solution of ($Me_3C$)$_2$PCl (3.0 g, 16.6 mmol, Aldrich) in 5.0 mL of $CH_2Cl_2$ was treated with $H_2O$ (0.5 g, 27.8 mmol) over a period of 5 min. The resulting reaction mixture was stirred at room temperature for an additional 30 min. Removal of solvent and excess $H_2O$ afforded 2.45 g (91% yield) of ($Me_3C$)PH(O)($CMe_3$). It was >95% pure by $^1H$ NMR and GC/MS. The pure product was obtained by sublimation (ca. 130° C./$10^{-3}$ torr), $^{31}P$ NMR (121 MHz, $CDCl_3$, $^1H$-decoupled): δ 69.8 ppm. $^{31}P$ NMR (121 MHz, $CDCl_3$, $^1H$-coupled): δ 69.8 (d, $J_{p\text{-}H}$=434.2 Hz). $^1H$ NMR (500 MHz, $CDCl_3$): δ 5.96 (d, $J_{p\text{-}H}$=434.7 Hz, 1H), 1.14 (d, $J_{p\text{-}H}$=156.4 Hz, 18H). $^{13}C$ NMR (125 MHz, $CDCl_3$): δ 33.8 ppm 14 (d, $J_{p\text{-}C}$=58.0 Hz), 25.6 ppm. MS: Calculated for $C_8H_{19}PO(M^+)$: 162.1. Found: 163.4 ($M^++H$).

Experiment 3

Synthesis of 2-PH(O)(i-Pr)-1, 5-$(MeO)_2C_6H_3$

A solution of $PBr_3$ (2.5 g, 9.2 mm) in 15 mL of pyridine was treated with 1,3-dimethoxybenzene (2.5 g, 18.1 mm) over a period of 5 min. The resulting mixture was then refluxed for 4 h to give the crude 1-dibromophosphino-2,4-dimethoxybenzene ($^{31}P$ NMR: δ 159.2 ppm). This compound was used directly for the next step without further purification. Next, polymer-supported secondary amines (10.0 g, 1.1 mmol/g, 11.0 mmol) was slowly added into the mixture above while stirring at room temperature for a period of 10 min. The resulting suspension was stirred at room temperature overnight before the solution was filtered off. The resin was washed with THF (50 mL), hexane (3×50 mL), $CH_2Cl_2$ (4×50 mL), and hexane (2×50 mL). The resulting resin was dried in vacuum overnight to yield the polymer-supported P(Br)-2,4-$(MeO)_2$-$C_6H_3$. $^{31}P$ NMR (122 MHz, $CDCl_3$): δ 153.8 ppm.

A suspension of this polymer-bound compound (2.0 g, 1.82 mmol, 0.908 mm/g) and I-PrMgBr (12.0 mmol, 1.0 M in THF solution) in 10 mL of THF was refluxed overnight before the solution was filtered off. The resulting resin was washed with THF (3×20 mL), $CH_2Cl_2$ (3×10 mL), $Me_2CHOH$ (2×10 mL), $THF/H_2O$ (70/30 volume ratio, 2×20 mL) and hexane (3×10 mL). The resin was dried in vacuum overnight. 31P NMR (122 MHz, $CDCl_3$): δ 60.7 ppm.

A suspension of polymer-bound P(i-Pr)-2,4-$(MeO)_2$-$C_6H_3$ (2.0 g, 1.876 mmol, 0.938 mm/g) and $H_2O$ (0.5 g, 28 mm) in 10 mL of THF was refluxed overnight before the resin was filtered off and washed with hexane (3×10 mL). Removal of solvents and excess $H_2O$ from the filtrates by vacuum afforded 100 mg (23% yield) of P(i-Pr)-2,4-$(MeO)_2$-$C_6H_3$. It was >95% pure by $^1H$ NMR and GC/MS. $^{31}P$ NMR (202 MHz, $CDCl_3$): δ 35.8 (s) ppm. $^{31}P$ NMR ($^1H$-coupled, 202 MHz, $CDCl_3$): δ 35.8 (d, $J_{P\text{-}H}$=485.8 Hz) ppm. $^1H$ NMR (500 MHz, $CDCl_3$): δ 7.57 (m, 1H), 7.25 (d, $J_{P\text{-}H}$=485.2 Hz, 1H), 6.48 (m, 1H), 6.37 (m, 1H), 3.76 (d, J=15.2 Hz, 3H), 3.70 (d, J=38.7 Hz, 3H), 2.18 (m, 1H), 1.12–0.81 (m, 6H). $^{13}C$ NMR (125 MHz, $CDCl_3$): 165.0, 161.8, 135.1, 105.6, 105.5, 98.2, 67.9, 55.6, 27.4, 14.5 ppm. MS: 229.2 (M+1).

EXAMPLES

A. Reactions of Amines with Aryl Halides

Example 1

In a drybox, 14.4 mg (0.087 mmol) of ($Me_3C$)$_2$PH(O) from Experiment 2, 20.0 mg (0.0218 mmol) of $Pd_2(dba)_3$ (dba=bis(dibenzylideneacetone)) and 4.0 mL of toluene were loaded into a reactor (20 mL) equipped with a magnetic stir bar. The resulting mixture was stirred at room temperature overnight. Next, 144 mg (1.5 mmol) of NaOtBu was added into the mixture above, followed by syringing 122 μl (1.2 mmol) of PhCl, and 100 μl (1.0 mmol) of piperidine into the reactor. The resulting mixture was refluxed for 5 h. The reaction mixture was then cooled to room temperature, chromatographed on silicon gel using ethyl acetate/hexane (5% volume ratio) as eluant. The eluate was concentrated by rotary evaporation followed by high vacuum to yield 82 mg (51% yield) of N-phenylpiperidine. It was >95% pure by $^1H$ NMR and GC/MS. $^1H$ NMR (500 MHz, $CDCl_3$): δ 7.15 (m, 2H), 6.84 (m, 2H), 6.72 (m, 1H), 3.06 (t, J=5.48 Hz, 4H), 1.61 (m, 4H), 1.48 (m, 2H) ppm. $^{13}C$ NMR (125 MHz, $CDCl_3$): d 152.3, 129.0, 119.2, 116.5, 50.7, 25.9, 24.43 ppm. MS: Calculated for $C_{11}H_{15}N(M^+)$: 161.3. Found: 162.3 ($M^++H$).

Example 2

The general procedure from Example 1 was followed using 4-chlorobenzo-trifluoride (650 mg, 3.6 mmol) and piperidine (258 mg, 3.0 mmol) with $Pd_2(dba)_3$ (55 mg, 0.081 mmol) and ($Me_3C$)$_2$PH(O) (21.0 mg, 0.126 mmol) and NaOtBu (432 mg, 4.5 mmol) in 6.0 mL of toluene. After 48 h, the reaction mixture was chromatographed with 5% ethyl acetate/hexane to give 161 mg (23% yield) of 4-piperidinobenzotrifluoride. It was >95% pure by $^1H$ NMR and GC/MS. $^1H$ NMR (500 MHz, $CDCl_3$): δ 7.36 (d, J=8.78 Hz, 2H), 6.82 (d, J=8.79 Hz, 2H), 3.18 (m, 4H), 1.60 (m, 4H), 1.54 (m, 2H) ppm. $^{13}C$ NMR (125 MHz, $CDCl_3$): d 153.7, 127.6, 126.3, 114.5, 49.2, 25.4, 24.2 ppm. MS: Calculated for $C_{12}H_{14}F_3N(M^+)$: 229.1. Found: 230.2 ($M^++H$).

Example 3

The general procedure from Example 1 was followed using chlorobenzene (135 mg, 1.2 mmol) and aniline (93 mg, 1.0 mmol) with $Pd_2(dba)_3$ (25 mg, 0.027 mmol) and $(Me_3C)_2PH(O)$ (7.0 mg, 0.042 mmol) and NaOtBu (144 mg, 1.5 mmol) in 2.0 mL of toluene. After 24 h, the reaction mixture was chromatographed with 5% ethyl acetate/hexane to give 51 mg (30% yield) of diphenylamine. It was >95% pure by $^1H$ NMR and GC/MS. $^1H$ NMR (500 MHz, $CDCl_3$): δ 7.18 (m, 4H), 6.99 (d, J=7.68 Hz, 4H), 6.84 (t, J=7.34 Hz, 2H), 5.59 (br, 1H) ppm. $^{13}C$ NMR (125 MHz, $CDCl_3$): d 143.1, 129.3, 120.9, 117.8 ppm. MS: Calculated for $C_{12}H_{11}N(M^+)$: 169.1. Found: 170.3 $(M^++H)$.

Example 4

The general procedure from Example 1 was followed using chlorobenzene (135 mg, 1.2 mmol) and piperidine (86 mg, 1.0 mmol) with $Pd_2(dba)_3$ (20 mg, 0.0218 mmol) and $(Me_2CH)PH(O)(Ph)$ from Experiment 1, (7.1 mg, 0.0424 mmol) and NaOtBu (144 mg, 1.5 mmol) in 2.0 mL of 1,2-dimethoxyethane. After 5 h, the reaction mixture was chromatographed with 5% ethyl acetate/hexane to give 17 mg (11% yield) of 4-phenylpiperidine. It was >95% pure by $^1H$ NMR and GC/MS. $^1H$ NMR (500 MHz, $CDCl_3$): δ 7.15 (m, 2H), 6.84 (m, 2H), 6.72 (m, 1H), 3.06 (t, J=5.48 Hz, 4H), 1.61 (m, 4H), 1.48 (m, 2H) ppm. $^{13}C$ NMR (125 MHz, $CDCl_3$): δ 152.3, 129.0, 119.2, 116.5, 50.7, 25.9, 24.4 3 ppm. MS: Calculated for $C_{11}H_{15}N(M^+)$: 161.3. Found: 162.3 $(M^++H)$.

Example 5

The general procedure from Example 1 was followed using 4-methyl-chlorobenzene (152 mg, 1.2 mmol) and piperidine (100 μl, 1.0 mmol) with $Pd_2(dba)_3$ (20 mg, 0.0218 mmol) and $(Me_3C)_2PH(O)$ (14.5 mg, 0.0878 mmol) and NaOtBu (144 mg, 1.5 mmol) in 3.0 mL of toluene. After 12 h, the reaction mixture was chromatographed with 5% ethyl acetate/hexane to give 106 mg (61% yield) of N-(4-methylphenyl)piperidine. It was >95% pure by $^1H$ NMR and GC/MS. $^1H$ NMR (500 MHz, $CDCl_3$): δ 6.92 (d, J=8.4 Hz, 2H), 6.72 (d, J=8.5 Hz, 2H), 2.95 (t, J=5.5 Hz, 4H), 2.13 (s, 3H), 1.58 (m, 4H), 1.43 (m, 2H) ppm. $^{13}C$ NMR (125 MHz, $CDCl_3$): δ 150.3, 129.5, 128.6, 116.9, 51.2, 25.9, 24.3, 20.3 ppm. MS: Calculated for $C_{12}H_{17}N(M^+)$: 175.1. Found: 176.1 $(M^++H)$.

Example 6

The general procedure from Example 1 was followed using PhCl (122 μl, 1.2 mmol) and p-toluidine (108 mg, 1.0 mmol) with $Pd_2(dba)_3$ (20 mg, 0.0218 mmol) and $(Me_3C)_2PH(O)$ (14.5 mg, 0.0878 mmol) and NaOtBu (144 mg, 1.5 mmol) in 3.0 mL of toluene. After 12 h, the reaction mixture was chromatographed with 5% ethyl acetate/hexane to give 80 mg (44% yield) of N-phenyl-p-toluidine. It was >95% pure by $^1H$ NMR and GC/MS. $^1H$ NMR (500 MHz, $CDCl_3$): δ 7.13 (t, J=7.91 Hz, 2H), 6.98 (m, 2H), 6.89 (m, 4H), 6.78 (t, J=7.32 Hz, 1H), 5.46 (s, br. 1H), 2.20 (s, 3H) ppm. $^{13}C$ NMR (125 MHz, $CDCl_3$): d 143.9, 140.3, 130.8, 129.8, 129.2, 120.2, 118.9, 116.8, 20.6 ppm. MS: Calculated for $C_{13}H_{13}N(M^+)$: 183.3. Found: 184.1 $(M^++H)$.

Example 7

The general procedure from Example 1 was followed using 4-chloroanisole (171 mg, 1.2 mmol) and piperidine (100 μl, 1.0 mmol) with $Pd_2(dba)_3$ (20 mg, 0.0218 mmol) and $(Me_3C)_2PH(O)$ (14.5 mg, 0.0878 mmol) and NaOtBu (144 mg, 1.5 mmol) in 4.0 mL of toluene. After 12 h, the reaction mixture was chromatographed with 5% ethyl acetate/hexane to give 128 mg (67% yield) of N-(4-methoxyphenyl)piperidine. It was >95% pure by $^1H$ NMR and GC/MS. $^1H$ NMR (500 MHz, $CDCl_3$): δ 6.81 (d, J=9.11 Hz, 2H), 6.72 (d, J=9.11 Hz, 2H), 3.65 (s, 3H), 2.92 (t, J=5.46 Hz, 4H), 1.60 (m, 4H), 1.46 (m, 2H) ppm. $^{13}C$ NMR (125 Mhz, $CDCl_3$): δ 153.5, 146.8, 118.6, 114.3, 55.4, 52.2, 26.1, 24.1 ppm.

Example 8

In the drybox, 20.0 mg (0.087 mmol) of $(Me_2CH)PH(O)(2,4-(MeO)_2C_6H_3)$ from Experiment 3, 20.0 mg (0.0218 mmol) of $Pd_2(dba)_3$ and 3.0 mL of dioxane were loaded into a reactor (20 mL) equipped with a magnetic stir bar. The resulting mixture was stirred at room temperature for 10 min. Next, 144 mg (1.5 mmol) of NaOtBu was added into the mixture above, followed by syringing 122 μl (1.2 mmol) of PhCl, and 100 μl (1.0 mmol) of piperidine into the reactor. The resulting mixture was refluxed for 8 h. The reaction mixture was then cooled to room temperature, chromatographed on silicon gel using ethyl acetate/hexane (5% volume ratio) as eluant. The eluate was concentrated by rotary evaporation followed by high vacuum to yield 59 mg (37% yield) of 1-phenylpiperidine. It was >95% pure by $^1H$ NMR and GC/MS. $^1H$ NMR (500 MHz, $CDCl_3$): δ 7.15 (m, 2H), 6.84 (m, 2H), 6.72 (m, 1H), 3.06 (t, J=5.48 Hz, 4H), 1.61 (m, 4H), 1.48 (m, 2H) ppm. $^{13}C$ NMR (125 MHz, $CDCl_3$): δ 152.3, 129.0, 119.2, 116.5, 50.7, 25.9, 24.43 ppm. MS: Calcd for $C_{11}H_{15}N(M^+)$: 161.3. Found: 162.3 $(M^++H)$.

The results of Examples 1–8 are summarized in Table 1 below.

TABLE 1

| Example | Phosphine oxide | Aryl compound | Amine | Product | Yield |
|---|---|---|---|---|---|
| 1 | $(Me_3C)_2PH(O)$ | chlorobenzene | piperidine | 1-phenylpiperidine | 51% |
| 2 | $(Me_3C)_2PH(O)$ | 4-chlorobenzotrifluoride | piperidine | 4-piperidinobenzotrifluoride | 23% |
| 3 | $(Me_3C)_2PH(O)$ | chlorobenzene | aniline | diphenylamine | 30% |
| 4 | $(Me_2CH)PH(O)(Ph)$ | chlorobenzene | piperidine | N-phenylpiperidine | 11% |
| 5 | $(Me_3C)_2PH(O)$ | 4-methylchlorobenzene | piperidine | N-(4-methylphenyl)piperidine | 61% |
| 6 | $(Me_3C)_2PH(O)$ | chlorobenzene | p-toluidine | N-phenyl-p-toluidine | 44% |
| 7 | $(Me_3C)_2PH(O)$ | 4-chloroanisole | piperidine | N-(4-methoxyphenyl)piperidine | 67% |
| 8 | $(Me_2CH)PH(O)(2,4-(MeO)_2C_6H_3)$ | chlorobenzene | piperidine | 1-phenylpiperidine | 37% |

B. Reactions of Arylboronic Acids with Aryl Halides

Example 9

In the drybox, 14.4 mg (0.087 mmol) of $(Me_3C)_2PH(O)$ from Experiment 2, 20.0 mg (0.0218 mmol) of $Pd_2(dba)_3$ and 4.0 mL of 1,4-dioxane were loaded into a reactor (20 mL) equipped with a magnetic stir bar. The resulting mixture was stirred at room temperature overnight. Next, 651 mg (2.0 MnMol) of $CsCO_3$ and 146.3 mg (1.2 mm) of PhB(OH)$_2$ were added into the mixture above, followed by syringing 122 μl (1.2 mmol) of PhCl into the reactor. The resulting mixture was refluxed for 24 h. The reaction mixture was then cooled to room temperature, chromatographed on silicon gel using ethyl acetate/hexane (5% volume ratio) as eluant. The eluate was concentrated by rotary evaporation followed by high vacuum to yield 163 mg (88% yield) of biphenyl. It was >95% pure by $^1$H NMR and GC/MS. $^1$H NMR (500 MHz, CDCl$_3$): δ 7.77 (d, J=7.75 Hz, 4H), 7.60 (t, J=7.65 Hz, 4H), 7.50 (t, J=7.38 Hz, 2H).ppm. $^{13}$C NMR (125 MHz, CDCl$_3$): δ 141.2, 128.7, 127.2, 127.1 ppm.

Example 10

The general procedure from Example 9 was followed using 4-methylchlorobenzene (152 mg, 1.2 mmol) and PhB(OH)$_2$ (1.2 mmol) with Pd$_2$(dba)$_3$ (20 mg, 0.0218 mmol) and (Me$_3$C)$_2$PH(O) from Experiment 2 (14.5 mg, 0.0878 mmol) and CsCO$_3$ (651 mg, 2.0 mmol) in 4.0 mL of 1,4-dioxane. After 24 h, the reaction mixture was chromatographed with 5% ethyl acetate/hexane to give 127 mg (63% yield) of 4-phenyltoluene. It was >95% pure by $^1$H NMR and GC/MS. $^1$H NMR (500 MHz, CDCl$_3$): δ 7.74 (d, J=7.50 Hz, 2H), 7.65 (d, J=8.05 Hz, 2H), 7.57 (m, 2H), 7.47 (m, 1H), 7.40 (m, 2H), 2.54 (s, 3H) ppm. $^{13}$C NMR (125 MHz, CDCl$_3$): δ 141.1, 138.3, 136.9, 129.4, 128.6, 126.9, 126.8, 21.0 ppm.

Example 11

The general procedure above was followed using 4-methylchlorobenzene (127 mg, 1.0 mmol) and PhB(OH)$_2$ (183 mg, 1.5 mmol) with Pd$_2$(dba)$_3$ (20 mg, 0.0218 mmol) and PhPH(O)(CHMe$_2$) from Experiment 1 (14.7 mg, 0.0874 mmol) and CsF (456 mg, 3.0 mmol) in 4.0 mL of 1,4-dioxane. After 12 h, the reaction mixture was chromatographed with 5% ethyl acetate/hexane to give 52 mg (31% yield) of 4-phenyltoluene. It was >95% pure by $^1$H NMR and GC/MS.

Example 12

In the drybox, 9.6 mg (0.058 mmol) of (Me$_3$C)$_2$PH(O) from Experiment 2, 13.3 mg (0.0145 mmol) of Pd$_2$(dba)$_3$ and 3.0 mL of 1,4-dioxane were loaded into a reactor (20 mL) equipped with a magnetic stir bar. The resulting mixture was stirred at room temperature overnight. Next, 143.0 mg (1.0 mm) of 4-chloroanisole, 182.9 mg (1.5 mm) of PhB(OH)$_2$ and 456 mg (3.0 mmol) of CsF were added into the reactor. The resulting mixture was refluxed for 24 h. The reaction mixture was then cooled to room temperature, chromatographed on silicon gel using ethyl acetate/hexane (5% volume ratio) as eluant. The eluate was concentrated by rotary evaporation followed by high vacuum to yield 179 mg (97% yield) of 4-phenylanisole. It was >95% pure by $^1$H NMR and GC/MS. $^1$H NMR (500 MHz, CDCl$_3$): δ 7.45 (m, 4H), 7.32 (m, 2H), 7.21 (m, 1H), 6.88 (d, J=8.72 Hz, 2H), 3.74 (s, 3H) ppm. $^{13}$C NMR (125 MHz, CDCl$_3$): δ 159.2, 140.8, 133.8, 128.7, 128.1, 126.7, 126.6, 114.2, 55.3 ppm.

Example 13

The general procedure from Example 12 was followed using 2-chloroanisole (143 mg, 1.0 mmol) and 4-MeC$_6$H$_4$B(OH)$_2$ (204 mg, 1.5 mmol) with Pd$_2$(dba)$_3$ (13.3 mg, 0.0145 mmol) and (Me$_3$C)$_2$PH(O) from Experiment 2 (9.6 mg, 0.058 mmol) and CsF (456 mg, 3.0 mmol) in 4.0 mL of 1,4-dioxane. After 24 h, the reaction mixture was chromatographed with 5% ethyl acetate/hexane to give 165 mg (83% yield) of 2-(4-methylphenyl)anisole. It was >95% pure by $^1$H NMR and GC/MS. $^1$H NMR (500 MHz, CDCl$_3$): δ7.32 (d, J=8.06 Hz, 2H), 7.18 (m, 2H), 7.10 (d, J=7.88 Hz, 2H), 6.92–6.84 (m, 2H), 3.67 (s, 3H), 2.28 (s, 3H) ppm. $^{13}$C NMR (125 Mhz, CDCl$_3$): δ 156.5, 136.5, 135.6, 130.7, 129.4, 128.7, 128.3, 120.8, 111.2, 55.5, 21.1 ppm.

Example 14

The general procedure from Example 12 was followed using 4-chloroanisole (143 mg, 1.0 mmol) and 4-MeOC$_6$H$_4$B(OH)$_2$ (228 mg, 1.5 mmol) with Pd$_2$(dba)$_3$ (13.3 mg, 0.0145 mmol) and (Me$_3$C)$_2$PH(O) from Experiment 2 (9.6 mg, 0.058 mmol) and CsF (456 mg, 3.0 mmol) in 3.0 mL of 1,4-dioxane. After 24 h, the reaction mixture was chromatographed with 5% ethyl acetate/hexane to give 213 mg (99% yield) of 4-(4-methoxyphenyl)anisole. It was >95% pure by $^1$H NMR and GC/MS. $^1$H NMR (500 MHz, CDCl$_3$): δ 7.38 (d, J=8.68 Hz, 4H), 6.86 (d, J=8.68 Hz, 4H), 3.74 (s, 6H) ppm. $^{13}$C NMR (125 MHz, CDCl$_3$): δ 158.7, 133.5, 127.7, 114.2, 55.3 ppm.

Example 15

In the drybox, 20.0 mg (0.0876 mmol) of (Me$_2$CH)PH(O)(2,4-(MeO)$_2$C$_6$H$_3$) from Experiment 3, 20 mg (0.0218 mm) of Pd$_2$(dba)$_3$ and 5.0 mL of 1,4-dioxane were loaded into a reactor (20 ml) equipped with a magnetic stir bar. The resulting mixture was stirred at room temperature overnight. Next, 143.0 mg (1.0 mm) of 4-chloroanisole, 228 mg (1.5 mm) of 4-MeOC$_6$H$_4$B(OH)$_2$ and 456 mg (3.0 mmol) of CsF were added into the reactor. The resulting mixture was refluxed for 60 h. The reaction mixture was then cooled to room temperature, chromatographed on silicon gel using ethyl acetate/hexane (5% volume ratio) as eluant. The eluate was concentrated by rotary evaporation followed by high vacuum to yield 213 mg (99% yield) of p-(4-methoxyphenyl)anisole. It was >95% pure by $^1$H NMR and GC/MS. $^1$H NMR (500 MHz, CDCl$_3$): δ8 7.38 (d, J=8.68 Hz, 4H), 6.86 (d, J=8.68 Hz, 4H), 3.74 (s, 6H) ppm. $^{13}$C NMR (125 MHz, CDCl$_3$): δ 158.7, 133.5, 127.7, 114.2, 55.3 ppm. Anal Calcd for C$_{14}$H$_{14}$O$_2$:C, 78.48; H, 6.59. Found: C, 78.44; H, 6.53.

The results of Examples 9–15 are summarized in Table 2 below.

TABLE 2

| Example | Phosphine oxide | Aryl compound | Acid | Product | Yield |
| --- | --- | --- | --- | --- | --- |
| 9 | (Me$_3$C)$_2$PH(O) | chlorobenzene | PhB(OH)$_2$ | biphenyl | 88% |
| 10 | (Me$_3$C)$_2$PH(O) | 4-methylchlorobenzene | PhB(OH)$_2$ | 4-phenyltoluene | 63% |
| 11 | PhPH(O)(CHMe$_2$) | 4-methylchlorobenzene | PhB(OH)$_2$ | 4-phenyltoluene | 31% |

TABLE 2-continued

| Example | Phosphine oxide | Aryl compound | Acid | Product | Yield |
|---|---|---|---|---|---|
| 12 | $(Me_3C)_2PH(O)$ | 4-chloroanisole | $PhB(OH)_2$ | 4-phenylanisole | 97% |
| 13 | $(Me_3C)_2PH(O)$ | 2-chloroanisole | $4\text{-}MeC_6H_4B(OH)_2$ | 2-(4-methylphenyl)-anisole | 83% |
| 14 | $(Me_3C)_2PH(O)$ | 4-chloroanisole | $4\text{-}MeOC_6H_4B(OH)_2$ | 4-(4-methoxyphenyl)-anisole | 99% |
| 15 | $(Me_2CH)PH(O)(2,4\text{-}(MeO)_2C_6H_3)$ | 4-chloroanisole | $4\text{-}MeOC_6H_4B(OH)_2$ | 4-(4-methoxyphenyl)-anisole | 99% |

What is claimed is:

1. A process to prepare arylamines of the formula $R^1$—$NR^2R^3$ comprising contacting an amine of the formula $HNR^2R^3$ with an aryl compound of the formula $R^1$—X in the presence of a catalytic amount of a coordination compound comprising one or more transition metals complexed to a phosphine oxide compound of the formula $HP(O)R^4R^5$, wherein X is a halogen;

$R^1$ is an optionally substituted aryl;

$R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

2. The process of claim 1 wherein $R^1$ is an optionally substituted phenyl.

3. The process of claim 2 wherein the transition metal is selected from Periodic Group VIII.

4. The process of claim 3 wherein $R^4$ and $R^5$ are independently selected from the group consisting of hydrocarbyl, substituted hydrocarbyl and heterocyclic, and wherein the transition metal is Pd.

5. The process of claim 4 wherein $R^2$ and $R^3$ are selected from the group consisting of hydrogen, optionally substituted aryl, and hydrocarbyl, and optionally $R^2$ and $R^3$ together form a ring.

6. The process of claim 5 wherein X is Cl.

7. The process of claim 6 wherein:

$R^1$ is selected from the group consisting of phenyl, 4-methylphenyl, 4-methoxyphenyl, and 4-trifluoromethylphenyl;

$R^2$ and $R^3$ are selected from the group consisting of hydrogen, phenyl, 4-methylphenyl, and together form a piperidyl ring; and $R^4$ and $R^5$ are selected from the group consisting of t-butyl, phenyl, i-propyl, and 2,4-methoxyphenyl.

8. A process to prepare biaryls of the formula $R^1$–$R^6$ comprising contacting a boronic acid of the formula $R^6$—B(OH)$_2$ with an aryl compound of the formula $R^1$—X in the presence of a catalytic amount of a coordination compound comprising one or more transition metals complexed to a phosphine oxide compound of the formula $HP(O)R^4R^5$, wherein X is a halogen;

$R^1$ is an optionally substituted aryl;

$R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

9. The process of claim 8 wherein $R^1$ is an optionally substituted phenyl.

10. The process of claim 9 wherein the transition metal is selected from Periodic Group VIII.

11. The process of claim 10 wherein $R^4$ and $R^5$ are independently selected from the group consisting of hydrocarbyl, substituted hydrocarbyl and heterocyclic, and wherein the transition metal is Pd.

12. The process of claim 11 wherein $R^6$ is an optionally substituted aryl.

13. The process of claim 12 wherein X is Cl.

14. The process of claim 13 wherein:

$R^1$ is selected from the group consisting of phenyl, 4-methoxyphenyl, 2-methoxyphenyl and 4-methylphenyl;

$R^6$ is selected from the group consisting of phenyl and 4-methoxyphenyl; and $R^4$ and $R^5$ are selected from the group consisting of t-butyl, phenyl, i-propyl, and 2,4-methoxyphenyl.

15. A method for the use of phosphine oxides as ligands for homogeneous catalysis of arylamines of the formula $R^1$—$NR^2R^3$ or biaryls of the formula $R^1$–$R^6$ comprising:

(1) preparing a coordination compound comprising one or more transition metals complexed to a phosphine oxide compound of the formula $HP(O)R^4R^5$, wherein X is a halogen;

$R^1$ is an optionally substituted aryl;

$R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring; and 2) contacting either (i) a boronic acid of the formula $R^6$—B(OH)$_2$ or (ii) an amine of the formula $HNR^2R^3$ with an aryl compound of the formula $R^1$—X in the presence of a catalytic amount of the coordination compound prepared in step (1) to form, respectively, arylamines of the formula $R^1$—$NR^2R^3$ or biaryls of the formula $R^1$–$R^6$.

* * * * *